United States Patent [19]

Roland

[11] Patent Number: 5,782,820
[45] Date of Patent: Jul. 21, 1998

[54] DISPOSABLE SEAL FOR VACUTAINER HOLDER

[76] Inventor: Patricia D. Roland, 4501 Rising Hill Rd., Altadena, Calif. 91001

[21] Appl. No.: 598,611

[22] Filed: Feb. 12, 1996

[51] Int. Cl.⁶ .................. A61B 19/00; A61B 5/00
[52] U.S. Cl. ............... 604/411; 600/577; 604/88
[58] Field of Search ................ 604/413, 411, 604/415, 905, 86–88; 128/764, 894; 600/577

[56] References Cited

U.S. PATENT DOCUMENTS

| | | | |
|---|---|---|---|
| 2,015,497 | 9/1935 | Scholl | 128/894 |
| 2,057,922 | 10/1936 | Scholl | 128/894 |
| 3,063,555 | 11/1962 | Hanington | 128/894 |
| 3,306,563 | 2/1967 | Soto | 604/413 |
| 4,155,350 | 5/1979 | Percarpio | 128/764 |
| 4,601,286 | 7/1986 | Kaufman | 128/894 |
| 5,611,792 | 3/1997 | Gustafsson | 604/411 |
| 5,637,107 | 6/1997 | Vaillencourt | 604/411 |

*Primary Examiner*—Mark O. Polutta
*Attorney, Agent, or Firm*—Willie Krawitz

[57] ABSTRACT

A disposable seal is provided at the connection between an insertion needle and associated VACUTAINER holder when drawing blood from a patient during a phlebotomy procedure. The seal comprises an outer absorbent layer, and successive layers of sealing plastic film, an adhesive layer, and a removable inner layer of film for exposing the adhesive layer for attachment to the VACUTAINER holder. Prior to use, the disposable seal is mounted on the VACUTAINER holder along the adhesive layer and the insertion needle is pierced through the sealing portion of the plastic film and threaded into the VACUTAINER holder. A portion of the sealing plastic layer of film is partially detached by the insertion needle and wraps around the threaded portion of the VACUTAINER holder to improve the seal between the needle, and any small amount of blood leakage will be absorbed by the outer absorbent layer of the seal. The VACUTAINER holder can then be reused, using standard sterilization procedures.

5 Claims, 1 Drawing Sheet

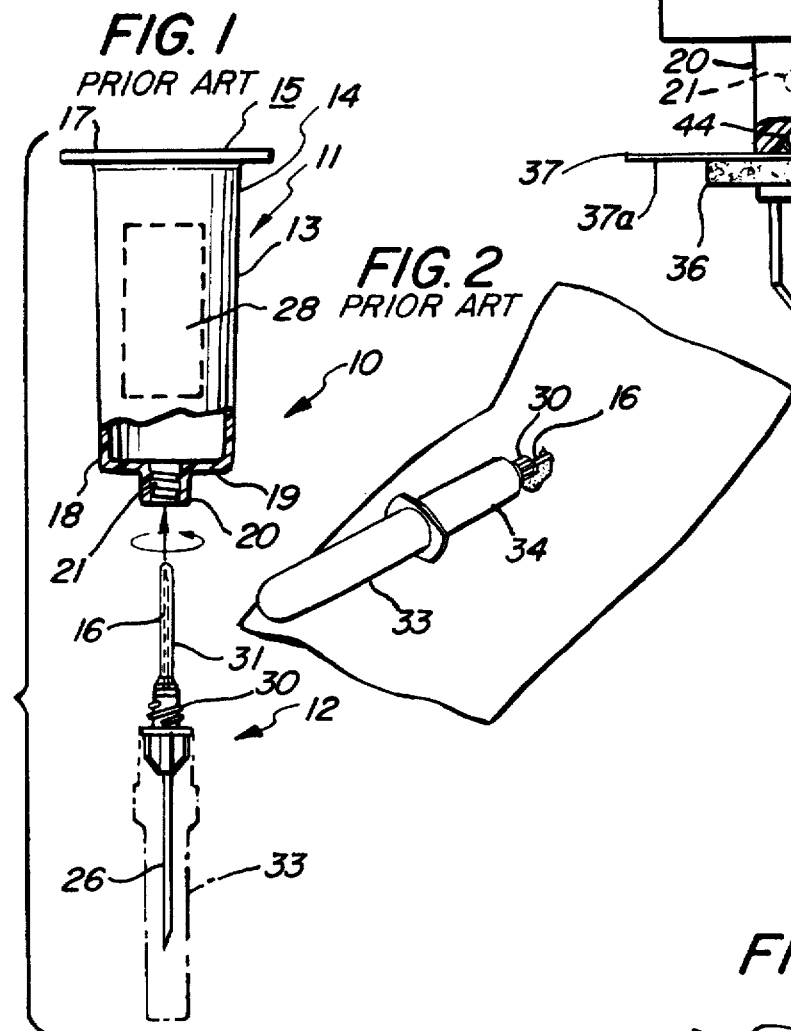
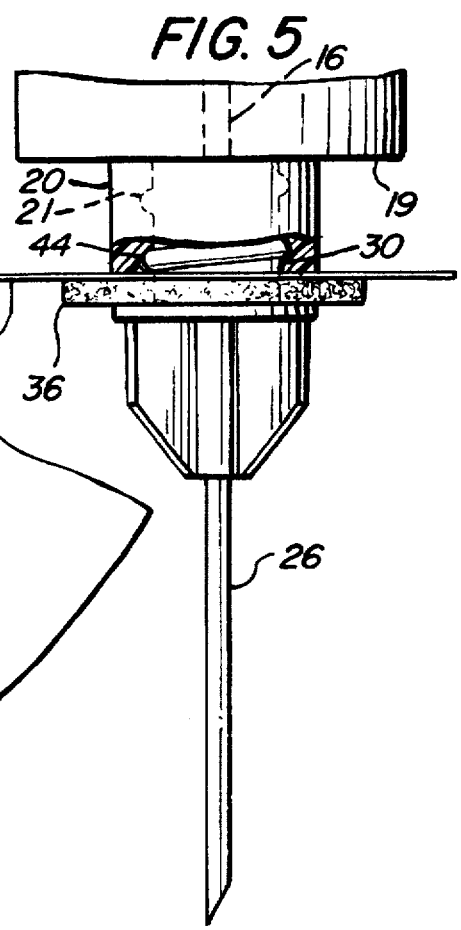
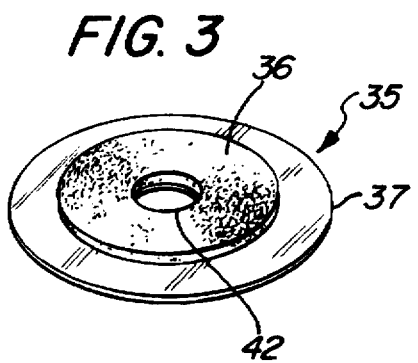
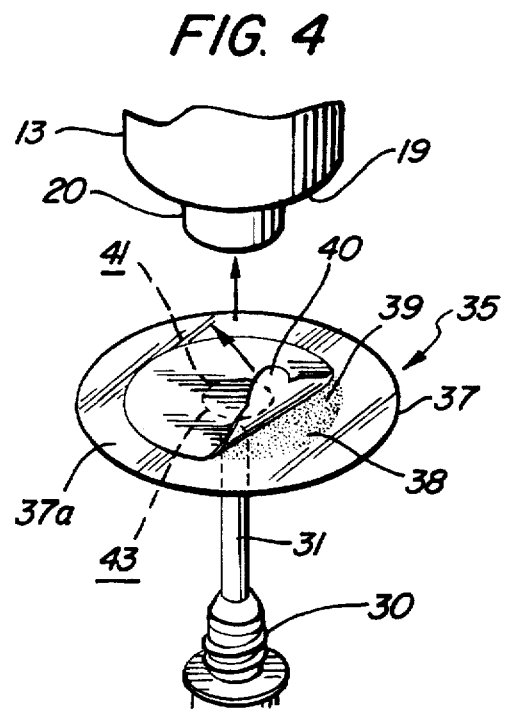

5,782,820

1

DISPOSABLE SEAL FOR VACUTAINER HOLDER

BACKGROUND OF THE INVENTION

This invention relates to a new and improved disposable seal for use between an insertion needle and a VACUTAINER holder and an assembly therewith, and for a method of using the seal in conjunction with the assembly.

Present VACUTAINER holders are frequently contaminated with blood resulting from a phlebotomy procedure, but it is difficult to determine if a particular blood sample contains a given disease. Hence, the user either discards the VACUTAINER holder since it may be dangerously heavily contaminated for effective sterilization, or the user may employ expensive sterilization procedures to salvage the VACUTAINER and reduce costs.

Typical publication disclosing VACUTAINER holders, and their use are U.S. Pat. Nos. 4,085,737; 4,643,199; 4,788,986; 4,790,827; 4,813,426; 4,822,343; 4,840,185; 4,892,107; 4,904,242; 5,066,287; 5,067,490; 5,086,780; 5,120,311; 5,131,405; 5,188,612; 5,222,505; 5,356,392; 5,374,250; and, 5,403,286.

Many of these patents describe complicated VACUTAINER holders used in a phlebotomy procedure, but none of these patents describe a device which is simple and inexpensive, and which are quick and easy to operate in terms of preventing or reducing blood contamination of the VACUTAINER holders.

THE INVENTION

According to the invention, a disposable seal is adhesively mounted on the VACUTAINER holder and adjacent the threaded connection used to engage an insertion needle. The seal comprises an outer absorbent layer, an inner layer of plastic film, an adhesive layer, and a removable cover for the adhesive layer. When the seal is pierced by the insertion needle, a portion of the inner layer of plastic film is ruptured and wraps around the threaded connection to improve the seal between the needle.

The threaded connections of presently designed VACUTAINER holders and the needle holder are both manufactured by an inexpensive injection molded process, and hence they tend to lack the necessary mechanical thread tolerances which are required to produce a high quality seal. However, when using the inexpensive plastic film as an added seal along the threaded connections, this compensates for the lack of thread tolerance and produces an effective and inexpensive seal. Also, it is quite easy to disengage and discard the insertion needle and the seal from the VACUTAINER threads following use, since the plastic film does not bond to the threads of either the needle holder or the VACUTAINER holder. Similarly, the plastic film can be easily peeled from the threads of the VACUTAINER holder to permit sterilization, and reuse following the phlebotomy or other blood taking procedure.

The outer absorbent layer of the seal is used to absorb any possible blood leakage and therefore provides additional protection against contamination of the VACUTAINER holder itself. Also, the absorption of blood reduces risking blood contamination in the vicinity of a patient, and this is important from the standpoint of health care workers. In effect, the disposable seal of the present invention enables the use of a simple VACUTAINER holder without the concurrent problems posed by blood leakage.

2

BRIEF DESCRIPTION OF THE DRAWINGS

FIG. 1 is an external, longitudinal view, partly in section of a prior art insertion needle and VACUTAINER holder in the process of being assembled;

FIG. 2 is an external, perspective view of a partially encased insertion needle prior to being removed from it's container for use;

FIG. 3 is an external, perspective view of a disposable seal of this invention;

FIG. 4 is an external, perspective view of the disposable seal shown in FIG. 3 prior to being adhesively secured to the VACUTAINER holder; and, FIG. 5 is an enlarged view in axial section showing an insertion needle holder threadably interconnected with the VACUTAINER holder and disposable seal, according to the invention.

DESCRIPTION OF THE PREFERRED EMBODIMENTS

A prior art pre-assembly 10 of a VACUTAINER holder 11 and an insertion needle holder 12 is shown in FIG. 1, and both holder 11 and 12 are typically constructed of an injection molded plastic such as polypropylene, nylon, pvc, etc., or other suitable sterilizable polymer. The VACUTAINER holder has a somewhat elongate shape providing a circular wall 13 defining at its distal end 14 an opening 15 to accommodate a VACUTAINER for connection with an insertion needle 16. An integrally formed shoulder portion 17 is provided for use with an injection syringe (not shown), if desired, instead of being used in conjunction with a VACUTAINER. At its proximal end 18, the circular wall 13 terminates in an integrally formed shoulder portion 19 and a central hollow connection stud 20 defining internal threads 21 for engagement with the needle holder 12.

As shown in FIG. 1, the insertion needle holder 12 comprises the proximal needle element 16 and a distal needle element 26 which are mounted within a plastic needle holder 27 at opposed ends of the needle holder. The proximal needle element is subsequently inserted into a VACUTAINER (not shown). An externally threaded portion 30 is defined midway along the needle holder to engage the internal threads 21 of VACUTAINER holder 11. As indicated, the distal needle element 26 is inserted into a patient to draw blood, and the proximal needle element 16 is inserted into a blood collection container 28 within VACUTAINER holder 11.

Protective elastomer sleeves, one sleeve 31 being shown, are used as temporary covers for the needles just prior to use, and these sleeves are removed immediately preceding a phlebotomy procedure. For more permanent storage, the insertion needle assembly 12 may be stored in plastic container halves 33 and 34 which encase the needle elements 16 and 26.

During use of the prior art assembly 10, shown in FIGS. 1 and 2, the proximal insertion needle 16 is threadably inserted to engage the VACUTAINER holder 11, and subsequent insertion into the blood collection container 28. The distal needle 26 is inserted into a patient to recover a blood sample, and the phlebotomy procedure is concluded. The problem with this procedure is that the external threads 30 of needle holder 27 and the internal threads 21 of the VACUTAINER holder usually do not have the dimensional tolerances required to form a suitably tight seal, given the tolerances of injection molded products of this type. Hence, there is a tendency to leak blood, albeit a small amount, from around the seal. But blood leakage can pose unacceptable problems of contamination due to unknown disease possibilities inherent in the blood of a patient. Hence, clinics and hospitals either discard the VACUTAINER holder, or employ sterilization procedures which must be overly rigorous to assure a sterile product, but in either case, this is a costly proposition.

FIGS. 3, 4 and 5 illustrate the disposable seal 35 of this invention assembled with a typical commercial phlebotomy needle in the VACUTAINER holder of FIGS. 1 and 2. FIG. 3 shows the seal 35 comprising an outer absorbent layer 36 of cotton or similar material adhesively secured to an inner layer of plastic film 37 such as about one (1) mil thick polyethylene film, saran, rubber, latex, etc. The film 37 is adhesively secured to an outer, double-sided adhesive layer 38, the outer side 39 of which is covered by a removable tear strip 40. A portion of film 37a extends outwardly from the adhesive and absorbent layers.

Centrally disposed registered holes 41 and 42 are defined on the absorbent layer 36 and the adhesive layer 38, and will expose a section 43 of the plastic film 37. As shown in FIGS. 4 and 5, when the tear strip 40 is removed, the outer side 39 of the adhesive layer can be attached to the shoulder portion 20 of VACUTAINER holder 11, and the holes 41 and 42 are positioned over the hollow connection stud 20.

When the insertion needle (or other mechanical means) is then pierced through the plastic layer of film 37, and through the holes 41 and 42, this will cause a portion 44 plastic of film from the exposed section 43 to be partially torn away. As shown in FIG. 5, when the threaded portion 30 of the needle holder 27 is then engaged with internal threads 21 of the stud 20, a portion 44 of plastic film will be wrapped around the engaging threads 21 and 30 to improve the seal against blood leakage. In addition, the outer portion 37a of film 37 prevents blood leakage from contacting the VACUTAINER holder by deflecting blood leakage through the registered holes 41, 42 and onto absorbent layer 36 where it is absorbed. If desired, a disinfectant such as I2, alcohol, betadine, etc., may be applied to the absorbent layer 36 to further reduce the possibility of infection.

When the phlebotomy procedure has concluded, the insertion needle holder 12 (with attached needles), and the seal are easily disengaged and removed from both the blood collection container 28 and VACUTAINER holder 11 and discarded, the VACUTAINER holder then being sterilized and reused.

The disposable seal 35 of this invention has a size range typically about 1"-2", and up to about 8" in diameter, the latter large size being useful to protect a user's hand. The seals may be stored in a sterile container in loose form, or stored on a roll with perforations between seals to facilitate detachment, while maintaining a reasonable degree of sterility.

The seal of this invention enables use of existing VACUTAINER holders and VACUTAINER technology, and also existing commercial phlebotomy needle systems. Seals of this invention reduce the amount of contaminated blood present from a phlebotomy procedure and the seals are simple to manipulate and use and are readily stored. The seals are also inexpensive and effective, and represent a simple solution for reducing the costs associated with either discarding large numbers of VACUTAINER holders, or for necessitating overly stringent sterilization procedures.

I claim:

1. An assembly of a holder for a blood collection device associated insertion needle and mounting device, and a disposable seal, the holder including a chamber portion and a proximal portion defining a threaded entry for engaging threads of the mounting device for the insertion needle, the disposable seal comprising:

a.) a base pad constructed of a blood absorbent material;

b.) an outer, adhesive layer defining at least one adhesive side;

c.) an inner layer of plastic film secured to the base pad by one side of the adhesive layer;

d.) holes defined by the base pad and the adhesive layer, the holes being aligned to expose a portion of the plastic film; whereby:

i. the holes are sized and aligned for mounting over the threaded entry of the holder;

ii. penetration by the needle and associated mounting device through the disposable seal and the exposed plastic film form a partially torn-away portion of plastic film;

iii. when the needle mounting device and associate needle penetrate the holes of the disposable seal and is threadably engaged with the entry threads, the torn-away plastic film is drawn into the entry of the holder and becomes wrapped around the entry threads, thereby improving the seal between the threads, and reducing blood leakage between the holder and the needle mounting device during subsequent use; and, iv. the plastic film can be removed from the threads to permit reuse of the holder.

2. The assembly of claim 1, in which the plastic layer of the disposible seal extends beyond the base pad, and blood leakage from the holder is deflected onto, and absorbed by the base pad.

3. The assembly of claim 1, in which the holes of the disposable seal are registered.

4. The assembly seal of claim 1, in which the base of the disposable seal pad includes a disinfectant.

5. The assembly seal of claim 1, in which the base pad of the disposable seal is cotton, and the plastic film is selected from the class consisting of polyethylene and saran.

* * * * *